US006857772B2

(12) United States Patent
Brukilacchio

(10) Patent No.: US 6,857,772 B2
(45) Date of Patent: Feb. 22, 2005

(54) HIGH PERFORMANCE LIGHT ENGINE

(75) Inventor: Thomas J. Brukilacchio, Reading, MA (US)

(73) Assignee: Innovations in Optics, Inc., Woburn, MA (US)

( * ) Notice: Subject to any disclaimer, the term of this patent is extended or adjusted under 35 U.S.C. 154(b) by 36 days.

(21) Appl. No.: 10/315,786

(22) Filed: Dec. 10, 2002

(65) Prior Publication Data

US 2004/0109331 A1 Jun. 10, 2004

(51) Int. Cl.[7] .............................. A61B 1/06; F21S 4/00; F21V 5/00; G02B 6/06

(52) U.S. Cl. ....................... 362/572; 362/235; 362/250; 362/345; 362/373

(58) Field of Search ................................ 362/572, 573, 362/574, 230, 234, 235, 250, 296, 345, 373

(56) References Cited

U.S. PATENT DOCUMENTS

| | | | |
|---|---|---|---|
| 4,964,025 A | 10/1990 | Smith | |
| 5,289,356 A | 2/1994 | Winston | |
| 5,335,152 A | 8/1994 | Winston | |
| 5,586,013 A | 12/1996 | Winston et al. | |
| 5,699,201 A | 12/1997 | Lee | |
| 5,816,693 A | 10/1998 | Winston et al. | |
| 5,899,557 A | 5/1999 | McDermott | |
| 6,149,283 A | 11/2000 | Conway et al. | |
| 6,200,002 B1 | 3/2001 | Marshall et al. | |
| 6,257,737 B1 | 7/2001 | Marshall et al. | |
| 6,601,985 B1 * | 8/2003 | Jesurun et al. | 362/572 |

OTHER PUBLICATIONS

Welford, W.T. and Winston, R., High Collection Nonimaging Optics, Academic Press, Inc., San Diego, 1989, pp. 213–215.

* cited by examiner

*Primary Examiner*—Stephen Husar
*Assistant Examiner*—Sharon Payne
(74) *Attorney, Agent, or Firm*—Francis J. Caufield

(57) ABSTRACT

A surgical lighting system including overhead surgical lights having integrating cavities which capture metal halide arc lamp optical energy and output spatially uniform optical energy to reflectors which direct the optic energy to a common surgical illumination region, a surgical light port system having illuminating ports, and a thermal dissipater. The surgical lighting system includes power back-up systems and light sources with multiple lamps that are automatically sequenced to provide constant surgical illumination.

8 Claims, 10 Drawing Sheets

HIGH PERFORMANCE LIGHT ENGINE

CROSS-REFERENCE TO RELATED APPLICATIONS

FIELD OF THE INVENTION

This invention relates to an optical system, and more particularly, to an optical system that provides constant white light to a region.

BACKGROUND OF THE INVENTION

Traditional illumination lamps suffer from poor color performance, poor intensity, and/or short usage life. Tungsten filament lamps, for example, while providing high intensity in the illumination pattern, emit a spectral distribution that is yellowish to the human visual system. In addition, tungsten filament lamps generate an enormous amount of heat, normally between 100 to 300 watts of heat energy, which results in raising the temperature of the surrounding environment.

Also, tungsten filament lamps have a low electrical to optical efficiency and, thus, require large amounts of electrical power to generate a high intensity illumination power. The higher amount of electrical power also contributes to the higher amount of heat generated by the tungsten filament lamp. Finally, tungsten lamps have a low life span, usually operating for about 500 hours.

Metal halide arc lamps provide a bluish color and come much closer to replicating white light as defined by the human visual system (e.g., more, for example, than tungsten does). However, metal halide arc lamps cannot be used in many applications because they cannot be hot-striked. That is, they cannot be cycled off and on without a significant restart time. A metal halide arc lamp that is cycled off then back on will not only fail but will also usually be damaged. More recent metal halide arc lamps have a much quicker on-off-on cycle time, however, they have low intensity illumination pattern.

An improved optical system is needed.

SUMMARY OF THE INVENTION

An embodiment of the invention provides a surgical lighting system including overhead surgical lights having integrating cavities which capture metal halide arc lamp optical energy and output spatially uniform optical energy to reflectors which direct the optic energy to a common surgical illumination region, a surgical light port system having illuminating ports, and a thermal dissipater which dissipates heat created by the generation of optical energy.

Another embodiment of the invention provides a surgical lighting system including electrical power back-up systems and light sources with multiple lamps that are automatically sequenced to provide constant surgical illumination.

BRIEF DESCRIPTION OF THE DRAWINGS

Other features of the invention will become apparent from the following detailed description considered in connection with the accompanying drawings. It is to be understood, however, that the drawings are designed as an illustration only and not as a definition of the limits of the invention.

In the drawings, wherein similar reference characters denote similar elements through the several views.

DETAILED DESCRIPTION OF THE PREFERRED EMBODIMENT

Figure 1:
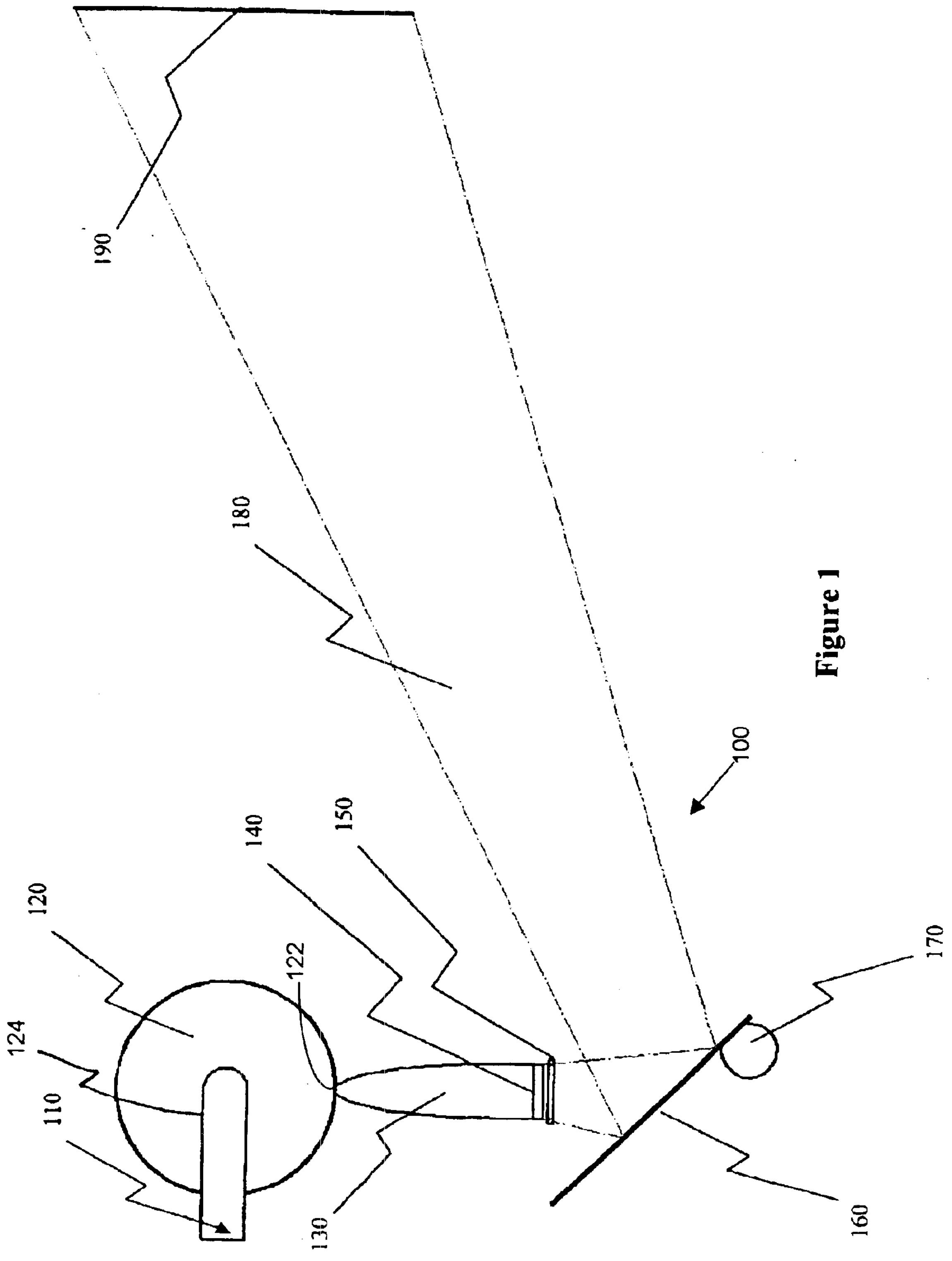
FIG. 1 illustrates an optical system according to an embodiment of the invention.

Referring to the drawings and in particular to FIGS. 1–10, there is shown the preferred embodiments of the invention.

FIG. 1 illustrates optical system 100 according to a preferred embodiment of the invention. The optical system 100 includes a light source 110, an integrating cavity 120, a concentrator 130, an optical filter 140, an intensity controller 150, a reflector 160, an illumination pattern controller 170, an illumination region 180, and an illumination pattern 190.

The light source 110 is optically attached to the integrating cavity 120 and emits optical energy which is captured by the integrating cavity 120. In a preferred embodiment of the invention, the light source is a high performance, high power, metal halide arc lamp. In an alternative embodiment, any light source that can provide sufficient optical energy to satisfy the requirements of the illumination pattern may be used.

In an alternative embodiment, the optical source includes a three lamp cluster where only one lamp would be at full capacity at any given time. When the lamp that is generating the optical energy falls below a performance threshold, a different lamp is automatically activated and the overall performance of the optical system is not altered.

In a preferred embodiment of the invention, the active lamp (the one that is generating optical energy) is monitored for time of operation. When the operation time nears the prescribed limit, the monitor will not allow the formerly active lamp (the lamp that has gone past the lamp life) to be turned on and, instead, turns on a second or different lamp.

In FIG. 1, the integrating cavity 120 is optically attached to the concentrators 130, and emits optical energy which is captured by the concentrator 130. In a preferred embodiment of the invention, the integrating cavity 120 is shaped in a sphere. In an alternative embodiment, the integrating cavity 120 is shaped in a torodial to increase the transfer of optical energy from the light source 110 to the concentrator 130. In an alternative embodiment, the integrating cavity 120 can be any shape which provides uniform spatial distribution of the optical energy to the entrance aperture of the non-imaging concentrator 130.

In a preferred embodiment of the invention, the integrating cavity 120 includes an entrance envelope 124 in which light source 110 is positioned. The insertion of the light source 110 into the integrating cavity 120 provides for increased transfer of optical energy.

In an alternative embodiment, entrance envelope 124 includes a filter to reflect ultra-violet optical energy. In an alternative embodiment of the invention, the entrance envelope 124 is a LTV absorptive glass. In an alternative embodiment of the invention, the glass is coated with a UV blocker. In an alternative embodiment, the entrance envelope 124 filters any optical energy wavelength.

In a preferred embodiment of the invention, the integrating cavity 120 includes exit ports 122 which mate to corresponding concentrators 130. In a preferred embodiment of the invention, the integrating cavity includes fifteen exit ports designed to optically attach to fifteen concentrators.

In a preferred embodiment of the invention, the integrating cavity is made of thermally conductive material which is coated on the inside with a highly reflective and efficiently scattering material.

In FIG. 1, the concentrator 130 is placed at each output port 122. A concentrator has an entrance aperture and an exit aperture. The entrance aperture is smaller than the exit aperture. The entrance aperture side of the concentrator is placed at the output port 122. A non-imaging concentrator converts light from an input angular distribution to an output angular distribution. In addition, a concentrator can capture optical energy over a full hemisphere ($2\pi$ steradians) angular distribution through the entrance aperture and then output the optical energy in a smaller angular distribution through the exit aperture.

In a preferred embodiment of the invention, the integrating cavity 120 outputs and the concentrator 130 captures optical energy with an angular distribution of 2 pi steradians (or a full hemisphere) at each exit port 122.

In a preferred embodiment of the invention, concentrator 130 is a compound parabolic concentrator, which is a particular form of a non-imaging concentrator. Non-imaging concentrators provide a high degree of light collection. The theoretical performance of a perfect non-imaging concentrator is greater than 96%. The ideal profile of a non-imaging concentrator is a compound parabola, which is referred to as a compound parabolic concentrator ("CPC"). The profile of a non-imaging concentrator 130 according to an embodiment of the invention is dictated by the angular requirements of the optical system. Thus, for example, when the concentrator is optically attached to a bundle of fibers the profile of the non-imaging concentrator produces an output angle which matches the acceptance angle of the optical fiber to have maximum transfer of optical energy. The reference Welford, Winston, "High Collection Nonimaging Optics", Academic Press, Inc. '89, ISBN 0-12-742885-2, which is incorporated herein by reference, provides a detailed discussion of nonimaging optics.

In an alternative embodiment of the invention, the non-imaging concentrator has a profile constructed with a high order polynomial surface representing the attributes of the non-imaging concentrator form. In an alternative embodiment of the invention, the aspheric sag equation is tuned to match an appropriate non-imaging concentrator. In an alternative embodiment, fifteen individual compound parabolic concentrators are coupled to the integrating cavity 120.

In a preferred embodiment of the invention, optical filter 140 is located at the exit aperture of the concentrator 130. Optical filter 140 transmits optical energy of a particular wavelength range and reflects optical energy of a different wavelength range. In a preferred embodiment of the invention, the optical filter 140 transmits optical energy of a particular wavelength range and absorbs optical energy of a different wavelength range. In a preferred embodiment of the invention, the optical filter removes optical energy that is not visible by the human visual system. In a preferred embodiment of the invention, the optical filter 140 is a band pass filter. In an alternative embodiment of the invention, optical system 100 omits the optical filter 140.

In an alternative embodiment of the invention, the optical filter 140 includes a filter which removes heat energy from the optical energy exiting the concentrator's exit aperture. In a preferred embodiment of the invention, an intensity controller 150 controls the amount of optical energy emitted to the illumination region.

In FIG. 1, in a preferred embodiment of the invention, a shutter wheel is positioned around the exit apertures of each concentrator 130 and after each optical filter 140. The same shutter aperture is present after each optical filter, which ensures that the illumination intensity will be uniformly controlled. In an alternative embodiment of the invention, the intensity can be non-uniformly controlled by mix changing the shutter aperture geometry for different shutter apertures in the shutter wheel. In an alternative embodiment of the invention, the speed of the intensity change is a function of the aperture geometry.

Rotating the shutter wheel will either increase or decrease optical energy output, depending on the geometric shape of the shutter. In an alternative embodiment of the invention, the inside of the shutter wheel is highly reflective so as to reflect the optical energy back into the optical system and removing thermal energy or heat from the forward components. In an alternative embodiment of the invention, optical system 100 omits the intensity controller 150.

In a preferred embodiment of the invention, a reflector segment 160 is used to direct the optical energy exiting through each intensity controller 150 into a unique illumination region 180. In a preferred embodiment, each concentrator 130 has a corresponding reflector segment 160 which produces a unique illumination region 180. In an alternative embodiment, reflector segment 160 is an ellipsoid.

Figure 2:
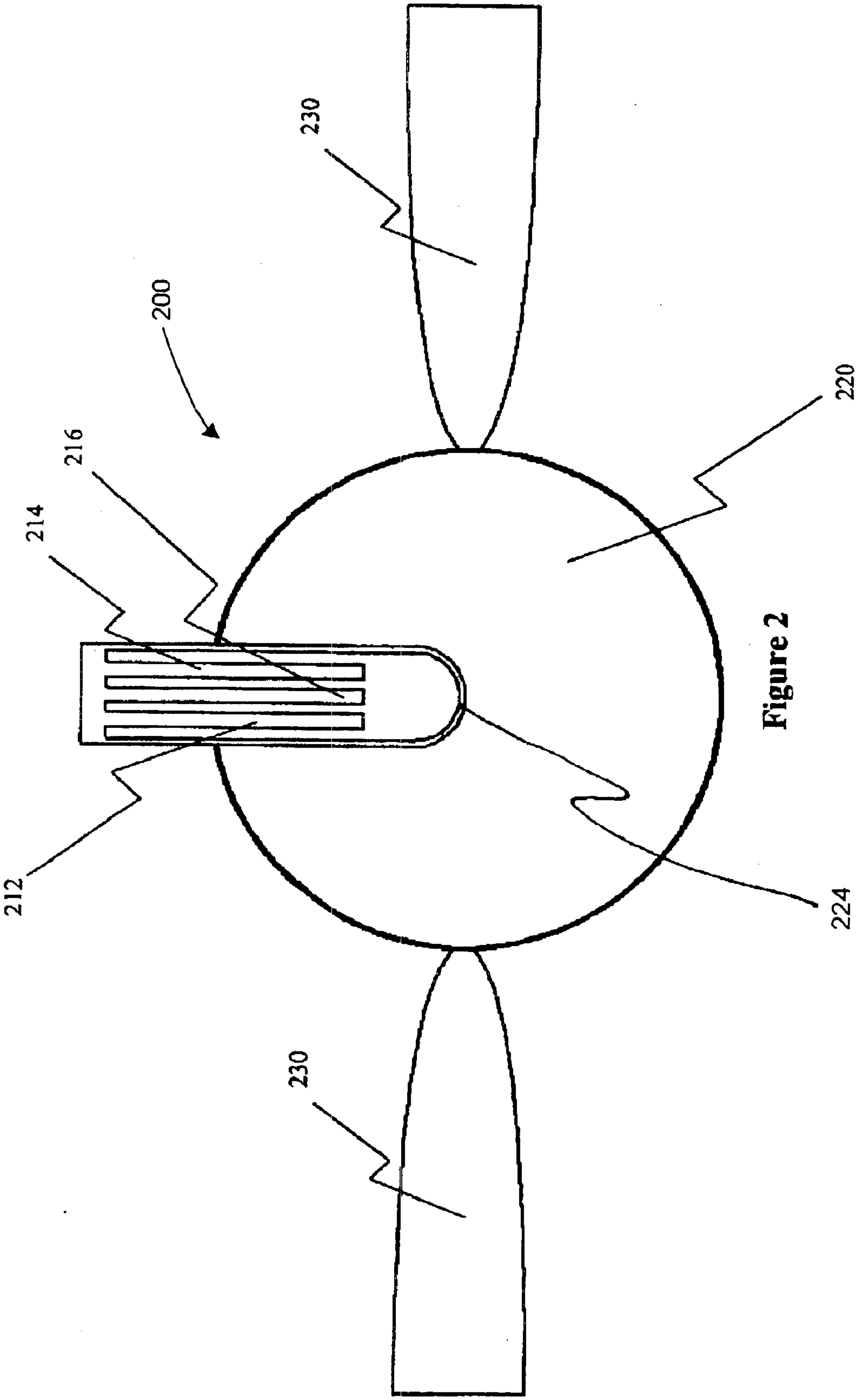
FIG. 2 illustrates a side view of an optical source component 200 a with according to an alternative embodiment of the invention.

FIG. 2 illustrates a side view of an optical source component 200 according to an alternative embodiment of the invention. Optical source component 200 includes the first lamp 212, second lamp 214, third lamp 216, the integrating cavity 220 and the multiple concentrators 230. The first lamp 212, the second lamp 214, and the third lamp 216 are each optically attached to the integrating cavity 220 which is optically attached to multiple concentrators 230.

Figure 3:
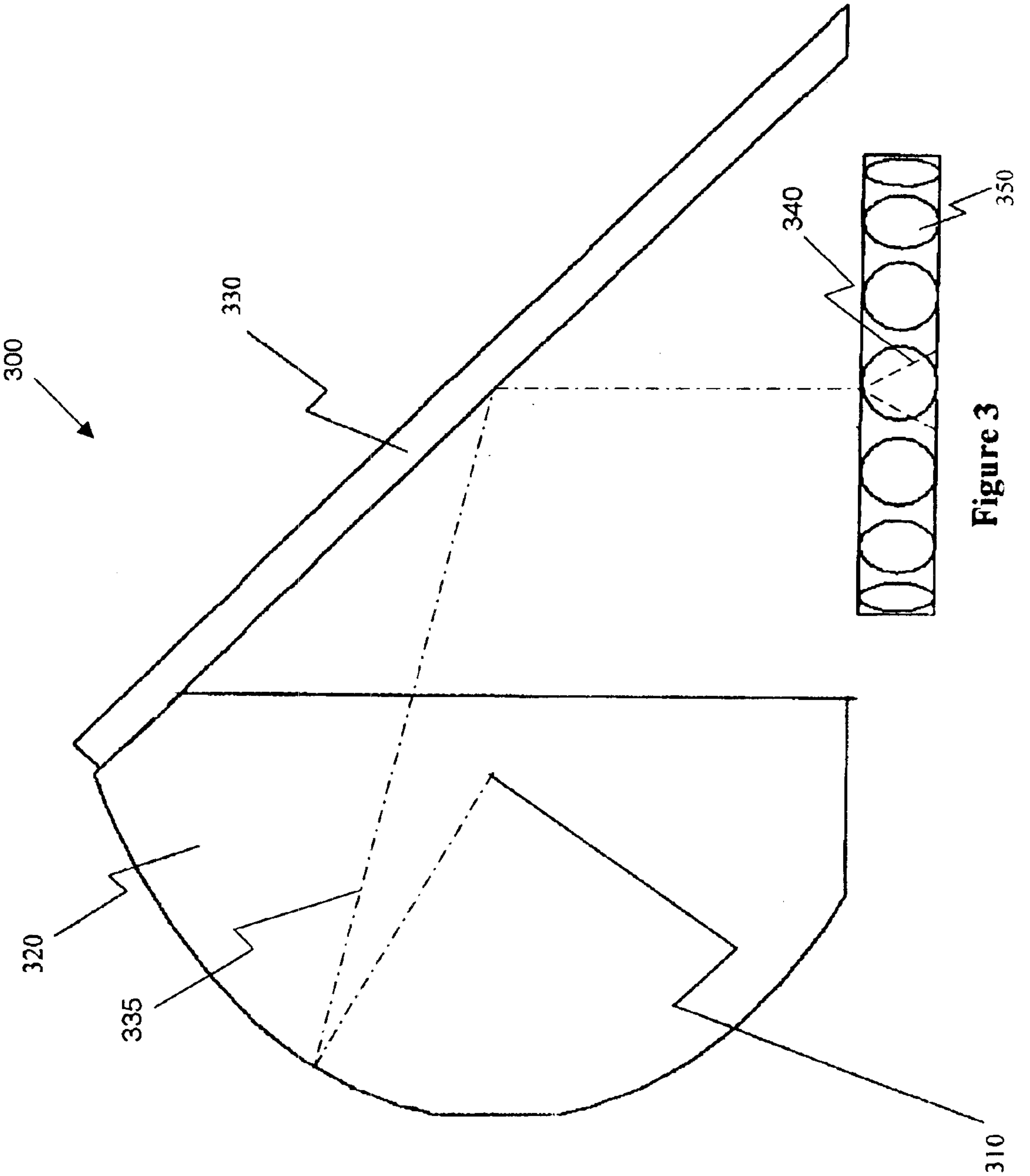
FIG. 3 illustrates an optical energy delivery device according to an alternative embodiment of the invention.

FIG. 3 illustrates an optical energy delivery device 300 according to an alternative embodiment of the invention. Optical energy delivery device 300 includes an optical source 310, a reflector 320, a mirror 330, an optical cone 340 and a concentrator 350.

In optical energy delivery device 300, the reflector 320 images the optical energy 335 from the optical source 310 to a mirror 330 which then directs the imaged optical energy to an optical cone 340. The optical cone directs the optical energy 335 to a concentrator 350. The concentrator then outputs spatially uniform optical energy. The optical (or light) source is placed at the first focus of an ellipse and imaged to the forty-five degree optical cone 340. The back reflector 320 is shaped in an elliptical form to image the optical energy 335. In an alternative embodiment, the mirror 330 is omitted and the reflector is moved so that the resulting image is received by the optical cone.

Figure 4B:
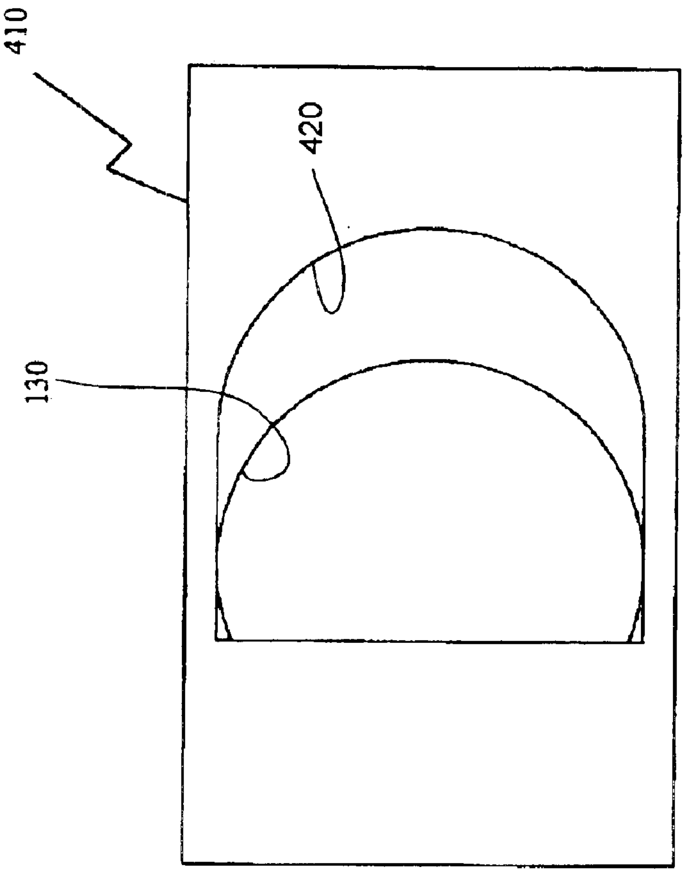
FIG. 4B illustrates a front view of a intensity controller partially obstructing the output aperture of a concentrator according to an alternative embodiment of the invention.
Figure 4A:
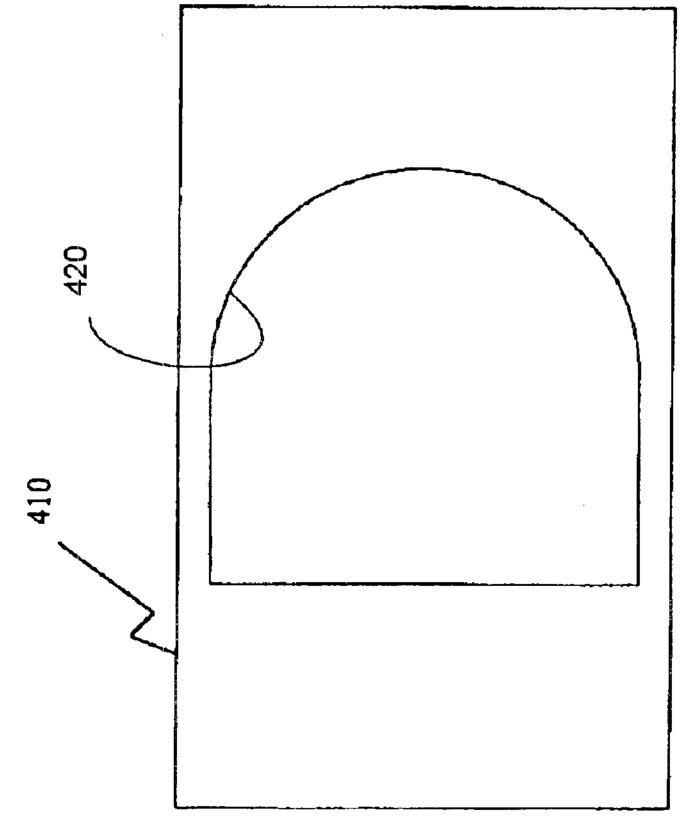
FIG. 4A illustrates a front view of a intensity controller according to an embodiment of the invention.

FIG. 4A illustrates a front view of a shutter 410 according to a preferred embodiment of the invention. Shutter 410 includes shutter aperture 420. Shutter aperture 420 can be any geometrical shape that gradually obstructs the path of optical energy when shutter 410 is moved. Shutter 410 is positioned after each optical filter 140 of each concentrator 130. FIG. 4B illustrates a front view of a shutter partially obstructing the output aperture of a concentrator according to an alternative embodiment of the invention.

Figure 5:
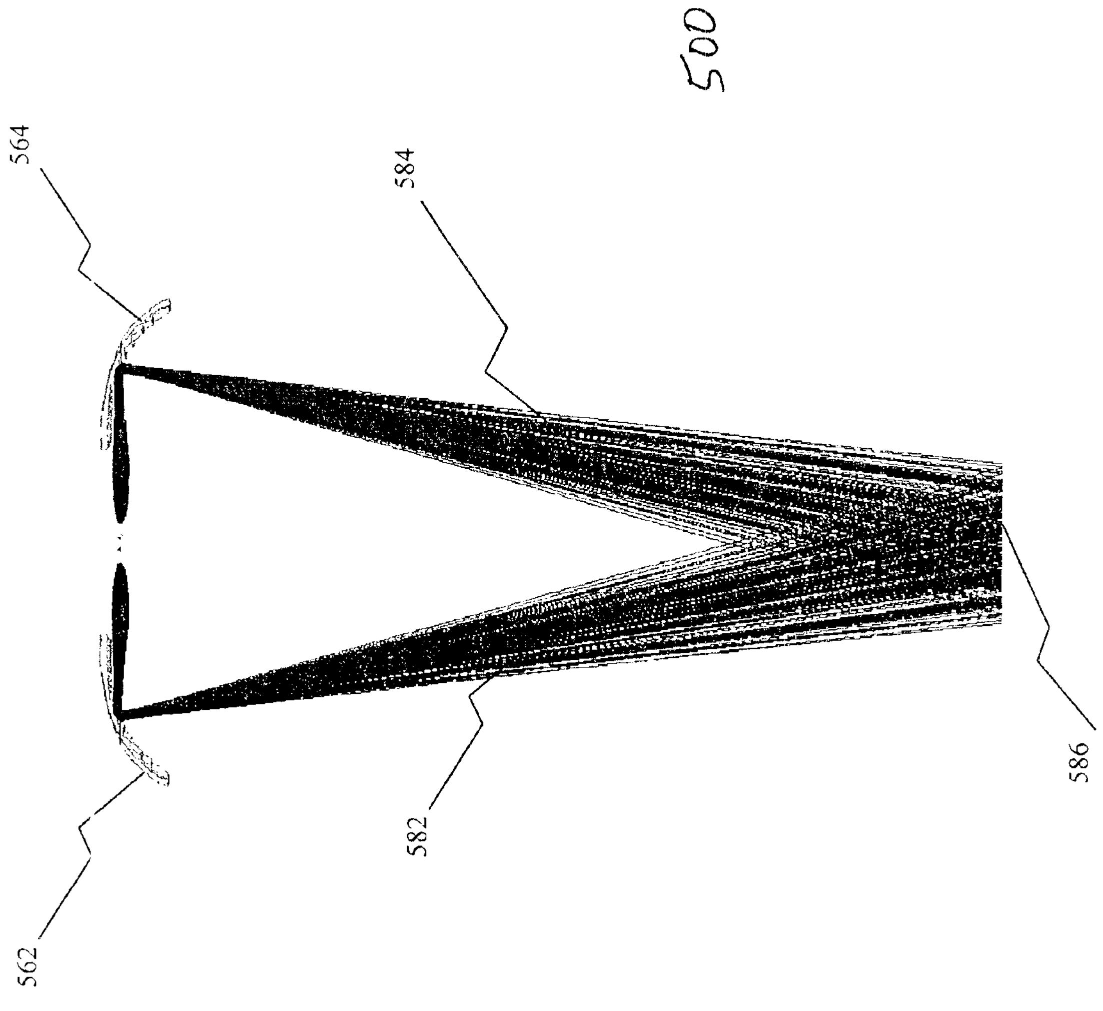
FIG. 5 illustrates the ray trace for a first reflector segment and a second reflector segment according to an alternative embodiment of the invention.

FIG. 5 illustrates the ray trace for a first reflector segment and a second reflector segment according to an alternative embodiment of the invention. The ray trace for a first reflector segment 562 corresponds to a first illumination regions 582 and second reflector segment 564 corresponds to a second illumination region 584. The plane where first illumination region 582 and second illumination region 584 fully overlap is the illumination pattern 586.

In FIG. 1, the shape of the reflector segments 160 affect the uniformity of the illumination region 180 and the partial overlapping region 186. Uniform illumination is important to reduce the effect of having a surgeon obscure the illumination pattern with a head, arm or object. In a preferred embodiment, the illumination pattern 190 has uniform illumination. In a preferred embodiment, each reflector segment 160 is identical. In a preferred embodiment, the reflector 160 is an elliptical in shape.

The shape of the reflector segment 160 helps to determine the uniformity of the illumination pattern 190. The shape of the reflector, which otherwise provides for uniform illumination, is established by determining what general reflector profile provides uniform illumination across the illumination pattern. A generic polynomial is constructed and modified while iterating through a series of ray-traces to find the optimum general reflector profile shape.

In an alternative embodiment of the invention, the optimum general reflector profile shape is further segmented into multiple reflecting facets. Faceting each reflector segment reduces the height of each segmented reflector. In addition, further partitioning of the entire reflector allows each reflector segment to be optimized for collection efficiency (e.g., from the collector) of the other axis (e.g., rotation about Y or the vertical axis).

Faceted reflector geometry ensures that the optical axis and the axis of rotation do not coincide thereby providing improved collection efficiency from each concentrator. The axis of rotation is given by the midpoint of the exit face of the non-imaging concentrator and the center of the pattern. This axis of rotation creates a non-rotationally symmetric main reflector.

In an alternative embodiment, each reflector segment 160 is faceted and the summation of all the faceted reflectors yield a pattern shape and an intensity in the pattern that satisfies the IEC 601-2-41 standards for major surgical lighting.

In a preferred embodiment of the invention, an illumination pattern controller 170 changes the size of the illumination pattern 190. An increase in illumination pattern size will decrease the illumination intensity over the illumination pattern. Conversely, a decrease in illumination pattern size will increase the illumination intensity of the illumination pattern.

In a preferred embodiment of the invention, the illumination pattern controller 170 is operated in conjunction with the intensity controller 150 to maintain uniform illumination pattern intensity while the illumination pattern is increasing or decreasing.

In a preferred embodiment of the invention, illumination pattern size is modified by tilting each reflector segment out of phase with its nearest neighbor. The illumination pattern size is increased when the mirror becomes more horizontal (e.g., when the illumination region extends somewhat vertically) and thereby shifts part of the reflected optical energy to a larger illumination pattern size while bringing some of the optical energy closer to the center of the illumination pattern. The illumination pattern size is decreased when the mirror becomes more vertical (e.g., when the illumination region extends somewhat vertically).

Figure 6:
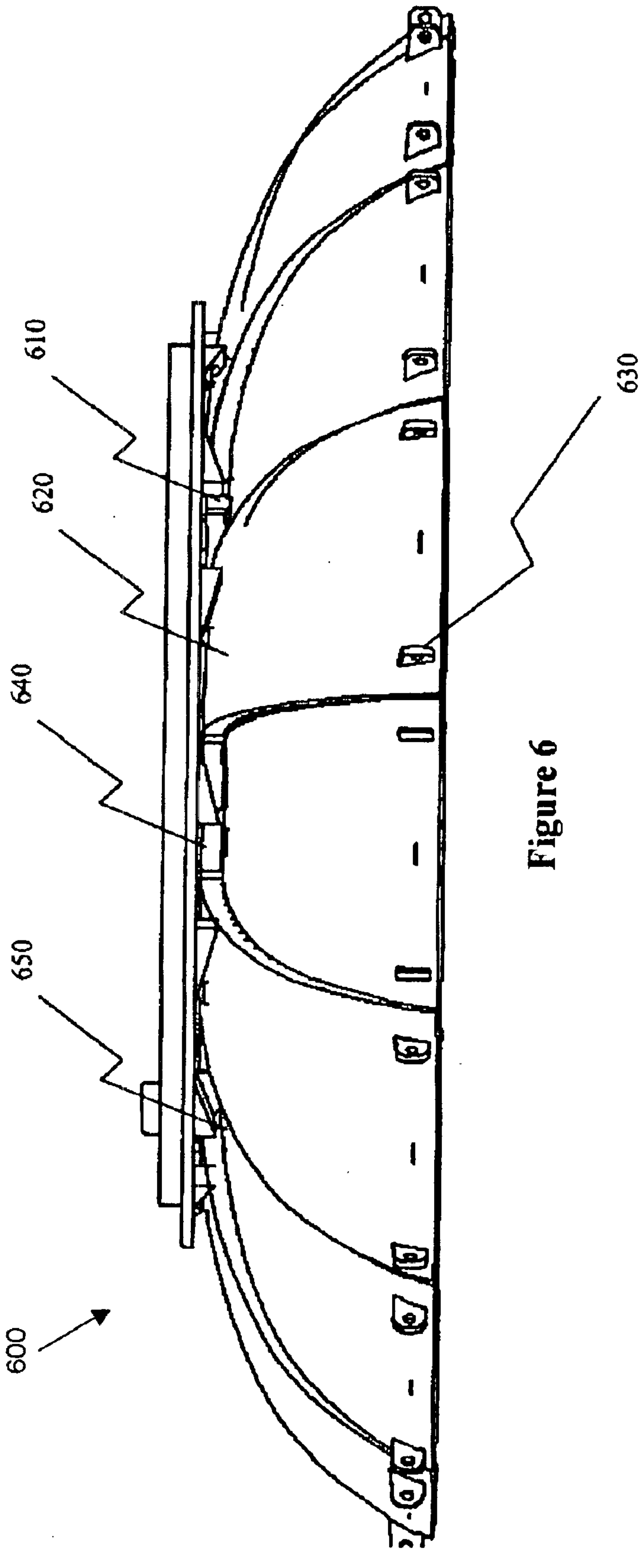
FIG. 6 illustrates the illumination pattern controller according to a preferred embodiment of the invention.

FIG. 6 illustrates the illumination pattern controller 600 according to a preferred embodiment of the invention. The illumination pattern controller 600 includes reflector protrusions 610 positioned on the top of each reflector segment 620 and away from each pivot 630, a reflector cam 640 positioned above each reflector segment, reflector cam protrusions 650 positioned to interact with each reflector protrusion 610 and attached to the reflector cam 640 when reflector cam 640 is rotated.

In a preferred embodiment, the reflector cam 640 is rotated by a small motor attached to a pinion gear (not shown). The pinion gear drives a radial rack gear on the reflector cam 640. In an alternative embodiment of the invention the reflector cam 640 rotates when the engine is energized.

In a preferred embodiment of the invention forced air dissipates thermal energy from the optical system 100. The light source 110 produces heat when generating optical energy. In addition, this heat is transferred to the integrating cavity. The heat from the optical system 100 heats the surrounding area.

Figure 7:
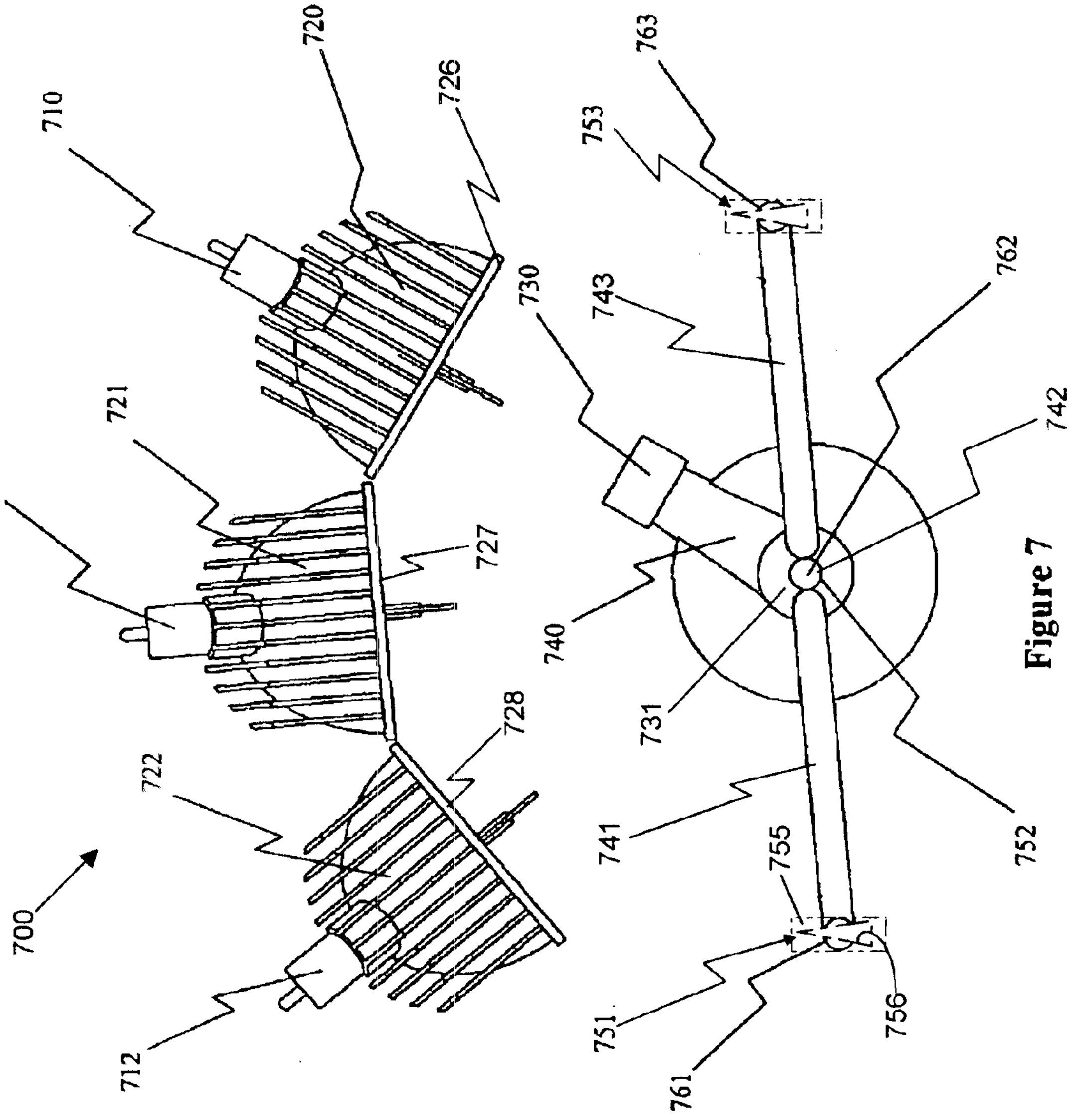
FIG. 7 illustrates a surgical light port system according to a preferred embodiment of the invention.

FIG. 7 illustrates a surgical light port system 700 according to a preferred embodiment of the invention. Surgical light port system 700 includes a first optical source 710, a second optical source 711 and a third optical source 712, a first reflector 720, a second reflector 721 and a third reflector 722, a three-into-one light guide 740 comprising an exit aperture 731 and an entrance head 730, a first output light pipe 741 with an exit aperture 761, a second output light pipe 742 with an exit aperture 762 and a third output light pipe 743 with an exit aperture 763, a first intensity controller 751, a second intensity controller (not shown), and a third intensity controller 753 over respectively first output light pipe aperture 761, second output light pipe aperture 762, and third output light pipe aperture 763.

At any given time, only one of the three optical sources 710, 711, 712 generate optical energy. When an optical source or lamp approaches its lamp life, the next time the surgical light port system is activated, a different lamp is automatically activated.

In a preferred embodiment of the invention, surgical light port system 700 includes an auxiliary power source and an electrical monitoring unit (not shown). The electrical power is monitored for continuity to the lamp control circuit by a monitor (not shown). When electrical power to the lamp is disrupted, the monitor switches the lamp control circuitry to an auxiliary power source thereby not permitting the active light source to cycle off. In a preferred embodiment of the invention, the auxiliary power source is a rechargeable battery. In an alternate embodiment of the invention, the auxiliary power is a hydrogen fuel cell.

In a preferred embodiment of the invention, first reflector 720 is located at the exit aperture of the first optical source 710, second reflector 721 is located at the exit aperture of the second optical source 711 and third reflector 722 is located at the exit aperture of the third optical source 712. Optical filters 726, 727, and 728 are located at the exits of reflectors 720, 721, 722, respectively. The optical filters 726, 727, and 728 transmit optical energy of a particular wavelength range and reflect optical energy of a different wavelength range.

In a preferred embodiment of the invention, the optical reflectors 720, 721, and 722 transmit optical energy of a particular wavelength range and absorb optical energy of a different wavelength range. In a preferred embodiment of the invention, the optical filters 726, 727, and 728 block optical energy that is not visible by the human visual system. In a preferred embodiment of the invention, the optical filters 726, 727, and 728 are band pass filters. In an alternative embodiment of the invention, the optical filters 726, 727, and 728 include a reflective filter which removes heat energy from the optical energy exiting the optical source. In an alternative embodiment of the invention, the optical filters 726, 727, and 728 include an absorptive filter which removes thermal energy from the optical energy exiting the optical source.

The active optical source (either first optical source 710, second optical source 711, or third optical source 712) generates optical energy and transmits the optical energy through the corresponding optical filter. In a preferred embodiment of the invention, a reflecting device is positioned behind and or around the optical source to direct additional optical energy to the optical filter. The optical energy that is transmitted through the optical filter enters the three-into-one light guide 740. The three-into-one light guide accepts optical energy from one light source (via the filter) and then directs the optical energy into three output light 741, 742, 743, each optical light guide has an exit aperture. The three-into-one light guide 740 is automatically indexed to receive optical energy from the active optical source when there is more than one optical source.

The first light pipe 741 delivers optical energy to the first output light pipe aperture 761, the second light pipe 742 delivers optical energy to the second output light pipe aperture 762, and the third light pipe 743 delivers optical energy to the third output light pipe aperture 763.

At each light pipe exit aperture of each output light pipe there is an intensity controller (751, 753). In a preferred embodiment, each intensity controller includes a slider 755 with a geometric cut out 756. In a preferred embodiment, the geometric cut out has a wedge shape. When the slider 755 is positioned upwards, the eclipsed area of the wedge grows larger, thereby increasing the optical energy at that output.

In a preferred embodiment, first intensity controller 751 closely positioned between first light guide 741 exit aperture and first output light guide 761,second intensity controller 752 closely positioned between second light guide 742 exit aperture and second output light guide 762, and third intensity controller 753 is closely positioned between first light guide 743 exit aperture and third output light guide 763. In a preferred embodiment of the invention, output light guides are very closely positioned next to the intensity controller.

In an alternative embodiment, optical output light guides (or ports) connect to for example, but not limited to surgical headlamps, endoscopes, or other medical devices requiring illumination.

Figure 8:
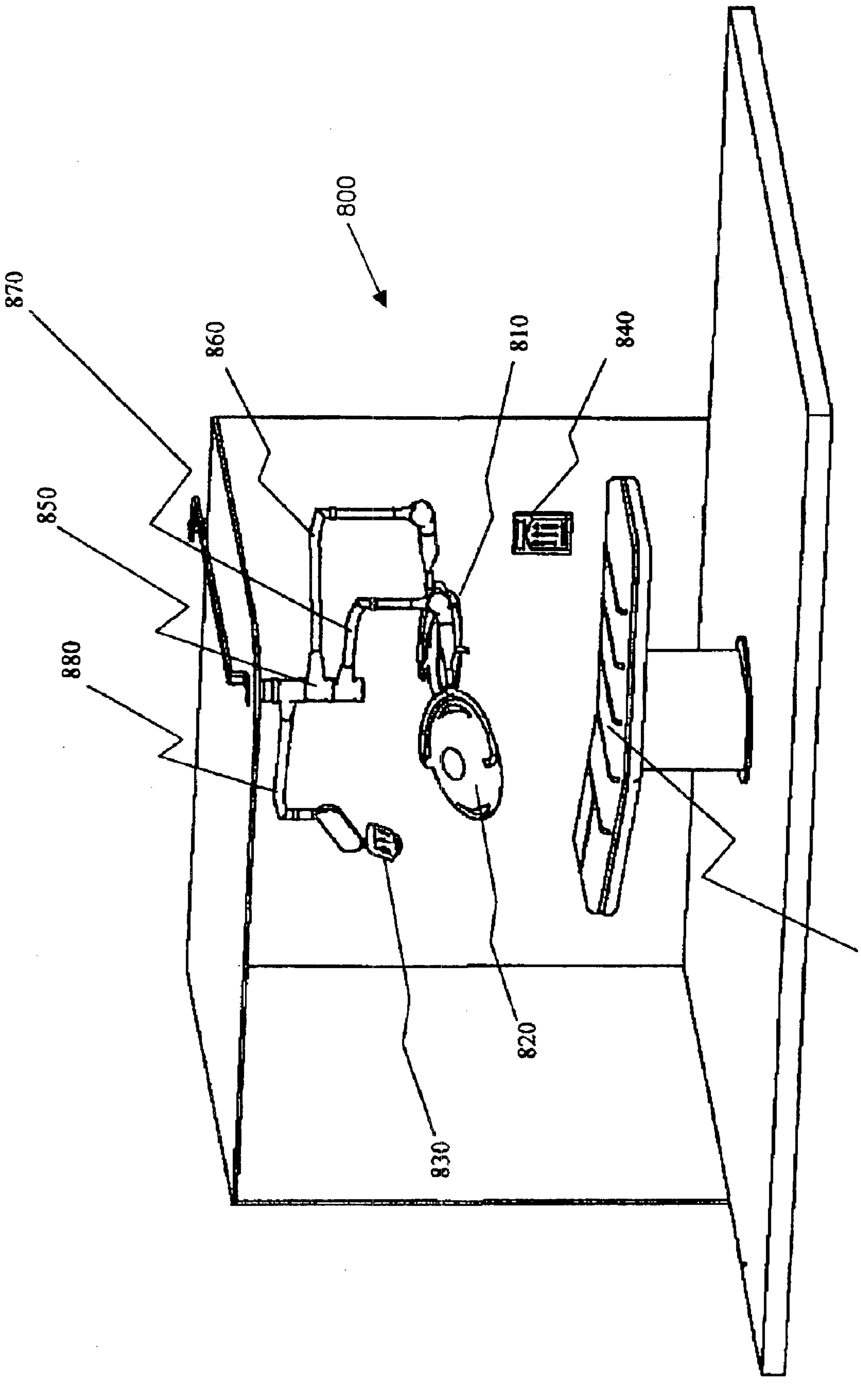
FIG. 8 illustrates a perspective of an overhead surgical lighting system according to a preferred embodiment of the invention.

FIG. 8 illustrates an overhead surgical lighting system 800 according to a preferred embodiment of the invention. The overhead surgical lighting system 800 includes a first optical system 810 and a second optical system 820, as illustrated FIG. 1 and described therein, a surgical lighting port system 830, as illustrated in FIG. 4 and described therein, a control box 840, a central column 850, a first optical system attaching arm 860, a second optical system attaching arm 870, a surgical lighting port system attaching arm 880, and a surgical illumination target 890. In an alternative embodiment of the invention, the surgical lighting system 800 includes a third optical system and a third optical system attaching arm (not shown).

The surgical lighting port system attaching arm 880 connects the surgical lighting port system 830 to the central column 850, the first optical system attaching arm 880 connects the first optical system 810 to the central column 850, the second optical system attaching arm 880 connects the first optical system 810 to the central column 850, and the central column attaches to the ceiling or wall. The control box 840 is communicatively connected to first optical system 810, the second optical system 820, and the surgical lighting port system 830.

In a preferred embodiment of the invention, there is an air passage from the first optical system 810, through the first optical system attaching arm 860, and through the central column 850. A fan (not shown) draws air from the overhead surgical lighting system 800 environment through said first optical system 810 and exhausts the air out the top (or side) of the central column.

In a preferred embodiment of the invention, there is an air passage from the second optical system 820, through the second optical system attaching arm 870, and through the central column 850. A fan (not shown) draws air from the overhead surgical lighting system 800 environment through said second optical system 820 and exhausts the air out the top of the central column. In an alternative embodiment of the invention, the fan (not shown) draws air from the overhead surgical lighting system environment through said second optical system and exhausts the air out of the side of the central column.

In a preferred embodiment of the invention, there is an air passage from the surgical lighting port system 830, through the surgical lighting port system attaching arm 880, and through the central column 850. A fan (not shown) draws air from the overhead surgical lighting system 800 environment through said surgical lighting port system 830 and exhausts the air out the top of the central column. In an alternative embodiment of the invention, the fan (not shown) draws air from the overhead surgical lighting system environment through said lighting port system and exhausts the air out of the side of the central column.

In a preferred embodiment, the drawn air is exhausted outside of the overhead surgical lighting system 800 environment. In an alternative embodiment, the drawn air is exhausted back into the room.

In an alternative embodiment, the integrating sphere is surrounded by a finned housing (not shown) to allow the flowing air to better dissipate heat.

The first optical system 810, the second optical system 820, and the surgical lighting port system can be controlled, modified and monitored from the control box 340.

The first optical system 810, emits first optical energy over and onto the illumination target 890. The second optical system 820, emits second optical energy over and onto the illumination target 890.

In an alternative embodiment of the invention, optical system 100 can be used in, for example but not limited to architectural illumination, machine vision systems, delivery of light via fiber to many locations, automotive and other general illumination systems, etc.

Figure 9:
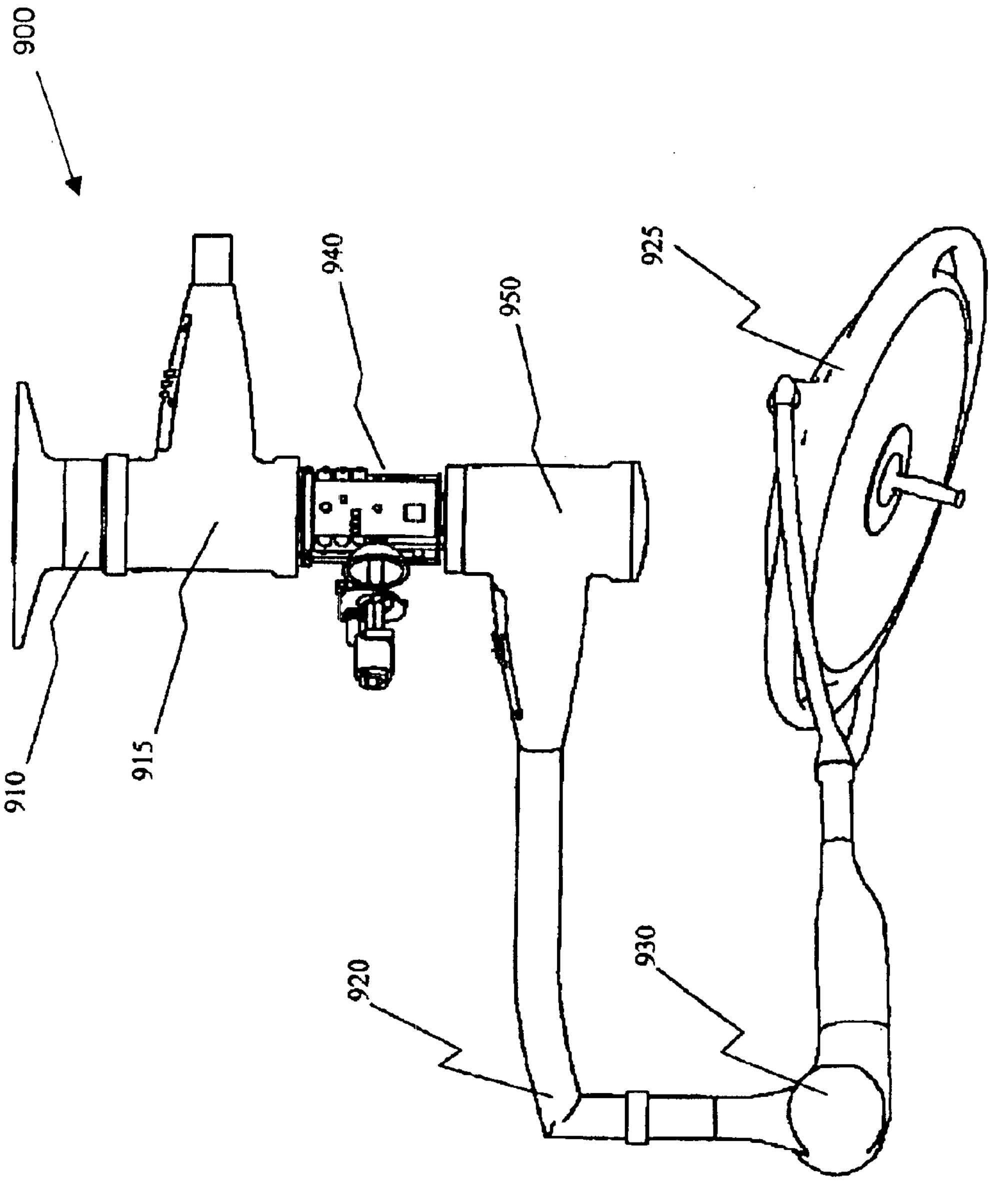
FIG. 9 illustrates a perspective of an overhead surgical lighting system according to a preferred embodiment of the invention.

FIG. 9 illustrates a perspective of an overhead surgical lighting system 900 according to an embodiment of the invention. Surgical lighting system 900 includes a center column 910, a hub 915, a support 920, and a light head 925. Light head 925 is supported by support 920 which attaches to hub 915. Hub 915 is a connecting geometric shape between the support 920 and the center column 910. In a preferred embodiment, the optic energy which emits from the light head is transferred from a distant light source. By locating the light source away from the light head, the heat associated with the light source is also located away from the light head. In an embodiment of the invention, the light source is located in hub 915. In another embodiment of the invention, the light source is located in support elbow 930. In another embodiment of the invention, the light source is located in hub 940, which is illustrated in FIG. 9 by a cut away view of the hub 940. In another embodiment of the invention, the light source is located in the elbow connector 950.

Figure 10:
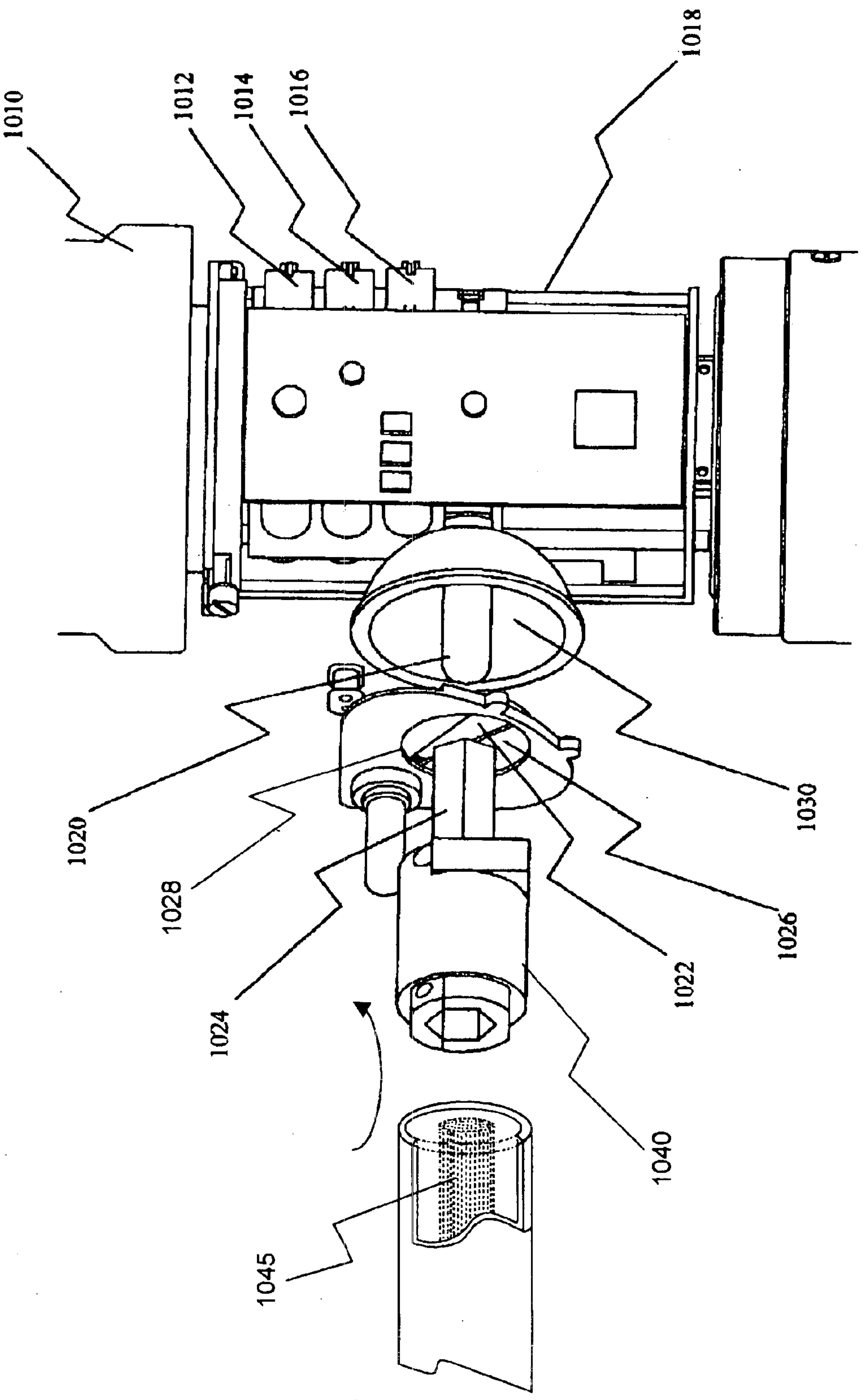
FIG. 10 illustrates a cut out perspective of a light source positioned in a hub of a surgical lighting system according to a preferred embodiment of the invention.

FIG. 10 illustrates a cut out perspective of a light source positioned in a hub of a surgical lighting system 1000 according to an embodiment of the invention. The surgical lighting system 1000 includes a center column 1010, multiple optical lamps 1012, 1014 and 1016 are located within column 1010. Lamp 1020 is positioned inside of the elliptical back reflector which is with the hub. The lamp exchanger 1018 mechanically positions a single lamp into the elliptical back reflector, which becomes the active lamp. The active lamp 1020 generates optical energy when power is received by the active lamp 1020. The lamp exchanger 1018 has room for multiple lamps and due to the automatic exchange mechanism prevents the surgical lighting system from engaging a lamp that has or will soon expire.

The optical source 1020, if a traditional metal halide or tungsten filament source emit a tremendous amount of thermal energy, 100 to 300 watts. This thermal energy is an unwanted byproduct in order to achieve the proper intensity for surgical applications. The surgical lighting system 1000 removes a substantial amount of the thermal energy (up to 95 percent depending on the light source) through the use of a heat absorptive filter 1022 positioned to interact with the optic energy created by the light source and an air cooling system that removes the thermal air out of the surgical environment by the use of a fan (not shown) positioned by the ceiling and, when operational, creates a flow of air through vents on the hub, through the light source, and other proximate optical elements nearby, and out the top of the center column, thereby minimizing any temperature variation in the surgical environment. The heat absorptive filter 1022 can be any type of optical filter that removes heat power from optical energy.

The optical energy that is transmitted past the optical filter 1022 is then interfaced into an optical mixing pipe 1024. The mixing pipe can be any optical element that has characteristics of spatially integrating optical energy.

In between the mixing pipe 1024 and the filter 1022 is an intensity controller 1028. The intensity controller controls the amount of optical energy that is received by the mixing pipe 1024. The intensity controller includes double shutter blades 1026 that can be manipulated to represent a specific intensity within the mixing pipe 1024. However, the intensity controller, by manipulating the optical energy received by the mixing pipe 1024, also controls the intensity of optical energy provided to the light head and, ultimately, the surgical region. To better reduce the amount of thermal energy, the intensity controller 1028 has highly reflective shutter blades 1026 to reflect the thermal power back into the center column 1010.

Once the optical energy is in the mixing pipe 1024, the optical energy is directed into a fiber bundle 1045. The fiber bundle optically attaches to the mixing pipe 1024 by an attaching element 1040. In an embodiment of the invention, the fiber bundle is hexagonal in shape. In an embodiment of the invention, the fiber bundle is continuous to the light head. The fiber bundle delivers the optical energy to the light head where it is then directed to a particular illumination region, pattern or target. By placing the light source in the hub, a continuous fiber bundle of about 12 feet can be used to deliver the optical energy. By using a continuous fiber bundle (i.e., with no optical element interactions or ninety degree turns) the surgical lighting system 1000 is able to provide surgical quality white light with only very minimal temperature increase.

In an alternative embodiment, the surgical lighting system 1000 is supported by an auxiliary power system that is enabled when the main or room power source is disabled. A back up power source allows the surgical lighting system to not cycle off. Another back up power source includes batteries, positioned within the center column or hub.

While the invention has been described in terms of preferred embodiments, those skilled in the art will recognize that the invention can be practiced with modifications within the spirit and scope of the appended claims.

What is claimed is:

1. A surgical light head device comprising:

a light source which provides optical energy;

an integrating cavity positioned to receive said optical energy, wherein said integrating cavity outputs spatially uniform optic energy:

a concentrator positioned to receive optic energy from said integrating cavity, wherein said concentrator includes an entrance aperture positioned toward said integrating cavity and an exit aperture positioned away from said integrating cavity, wherein said entrance aperture is smaller than said exit aperture, wherein said concentrator angularly aligns optical energy received from said integrating cavity creating aligned optical energy, and wherein said concentrator outputs aligned optical energy through said exit aperture;

an optic filter positioned to receive optical energy from said concentrator, wherein said optical fiber reflects optical energy creating reflected optical energy, wherein said optical filter transmits optical energy creating transmitted optical energy;

a reflector positioned to receive said transmitted optical energy, wherein said reflector reflects said transmitted optical energy to an illumination region, wherein said illumination region includes an illumination pattern;

an intensity controller positioned between said reflector and said optical filter, wherein said intensity controller controls the amount of optical energy received by said reflector; an illumination pattern controller positioned to control a of said illumination pattern; and a heat dissipater positioned to dissipate heat generated from said light source.

2. A surgical light head device comprising:

a light source which provides optical energy;

an integrating positioned to receive said optical energy, wherein said integrating cavity outputs spatially uniform optic energy;

a first concentrator positioned to receive optical energy from said integrating cavity, wherein said first concentrator includes a first entrance aperture positioned toward said integrating cavity and a first exit aperture positioned away from said integrating cavity, wherein said first entrance aperture is smaller than said first exit aperture, wherein said first concentrator angularly aligns optic energy received from said integrating cavity creating first aligned optical energy, and wherein said first concentrator outputs first aligned optical energy through said first exit aperture;

a first optic filter positioned to receive optical energy from said first concentrator, wherein said first optical filler reflects optical energy creating first reflected optical energy and wherein said first optical filler transmits optical energy creating second transmitted optical energy;

a first reflector positioned to receive said first transmitted optical energy wherein said first reflector reflects said first transmitted optical energy to a first illumination region and wherein said illumination region includes a first illumination pattern;

a first intensity controller positioned between said first reflector and said first optical filter, wherein said first intensity controller controls an amount of optical energy received by said first reflector;

a first illumination pattern controller positioned to control a size of said first illumination pattern;

a second concentrator positioned to receive optical energy from said integrating cavity, wherein said second concentrator includes a second entrance aperture positioned toward said integrating cavity and a second exit aperture positioned away from said integrating cavity, wherein said second entrance aperture is smaller than said second exit aperture, wherein said second concentrator angularly aligns optic energy received from said integrating cavity creating second aligned optical energy, and wherein said second concentrator outputs second aligned optical energy through said second exit aperture;

a second optic filter positioned to receive optical energy from said second concentrator, wherein said second optical filter reflects optical energy creating second reflected optical energy, wherein said first optical filler transmits optical energy creating second transmitted optical energy;

a second reflector positioned to receive said second transmitted optical energy wherein said second reflector reflects said second transmitted optical energy to a second illumination region wherein said illumination region includes a second illumination pattern;

a second intensity controller positioned between said second reflector and said second optical filter wherein said second intensity controller controls an amount of optical energy received by said second reflector;

a second illumination pattern controller positioned to control a size of said second illumination pattern; and a heat dissipater positioned to dissipate heat generated from said light source, wherein said first illumination region overlaps with said second illumination region, wherein said first illumination pattern overlaps with said second illumination pattern.

3. A surgical light head device comprising:

a light source which provides optical energy;

a back reflector positioned to receive said optical energy wherein said back reflector outputs imaged optical energy;

an optical cone positioned to receive optical energy from said back reflector, wherein said optical cone outputs spatially uniform optic energy;

a plurality of concentrators positioned to receive optic energy from said optical cone, wherein each concentatrator of said plurality of concentrators includes a corresponding entrance aperture positioned toward said optical cone and a corresponding exit aperture positioned away from said optical cone, wherein said corresponding entrance aperture is smaller than said corresponding exit aperture, wherein said each concentrator angularly aligns optical energy received from said optical cone creating aligned optical energy, and wherein said each concentrator outputs aligned optical energy through said corresponding exit aperture;

an optic filter positioned to receive optical energy from said each concentrator, wherein said optical filter reflects optical energy creating reflected optical energy, wherein said optical filter transmits optical energy creating transmitted optical energy;

a reflector positioned to receive said transmitted optical energy wherein said reflector reflects said transmitted optical energy to an illumination region, wherein said illumination region includes an illumination pattern;

an intensity controller positioned between said reflector and said optical filter, wherein said intensity controller controls the amount of optical energy received by said reflector; an illumination pattern controller positioned to control a size of said illumination pattern; and a heat dissipater positioned to dissipate heat generated from said light source.

4. A surgical light head device comprising:

a light source which provides optical energy;

a back reflector positioned to receive said optical energy wherein said back reflector outputs imaged optical energy;

an optical cone positioned to receive optical energy from said back reflector, wherein said optical cone outputs spatially uniform optic energy;

a first concentrator positioned to receive optical energy from said optical cone, wherein said first concentrator includes a first entrance aperture positioned toward said optical cone and a first exit aperture positioned away from said optical cone, wherein said first entrance aperture is smaller than said first exit aperture, wherein said first concentrator angularly aligns optic energy received from said optical cone creating first aligned optical energy, wherein said first concentrator outputs first aligned optical energy through said first exit aperture;

a first optic filter positioned to receive optical energy from said first concentrator, wherein said first optical filter reflects optical energy creating first reflected optical energy, wherein said first optical filter transmits optical energy creating second transmitted optical energy;

a first reflector positioned to receive said first transmitted optical energy wherein said first reflector reflects said first transmitted optical energy to a first illumination region, wherein said illumination region includes a first illumination pattern;

a first intensity controller positioned between said first reflector and said first optical filter wherein said first intensity controller controls an amount of optical energy received by said first reflector;

a first illumination pattern controller positioned to control a size of said first illumination pattern;

a second concentrator positioned to receive optical energy from said optical cone, wherein said second concentrator includes a second entrance aperture positioned toward said optical cone and a second exit aperture positioned away from said optical cone, wherein said second entrance aperture is smaller than said second exit aperture, wherein said second concentrator angularly aligns optic energy received from said optical cone creating second aligned optical energy, wherein said second concentrator outputs second aligned optical energy through said second exit aperture;

a second optic fitter positioned to receive optical energy from said second concentrator, wherein said second optical filter reflects optical energy creating second reflected optical energy, wherein said first optical filter transmits optical energy creating second transmitted optical energy;

a second reflector positioned to receive said second transmitted optical energy, wherein said second reflector reflects said second transmitted optical energy to a second illumination region, wherein said illumination region includes a second illumination pattern;

a second intensity controller positioned between said second reflector and said second optical filter wherein said second intensity controller controls an amount of optical energy received by said second reflector;

a second illumination pattern controller positioned to control a size of said second illumination pattern; and a heat dissipater positioned to dissipate heat generated from said light source, wherein said first illumination region overlaps with said second illumination region, and wherein said first illumination pattern overlaps with said second illumination pattern.

5. An surgical lighting port system comprising:

a light source providing optical energy;

a back reflector positioned to reflect said optical energy;

an optic filter positioned to receive said optical energy, wherein said optic filter reflects optical energy creating reflected optical energy, wherein said optic filter transmits optical energy creating transmitted optical energy;

a light guide positioned to receive said transmitted optical energy, wherein said light guide outputs said optical energy creating light guide optic energy;

a port light guide positioned to receive said light guide optic energy, wherein said port light guide outputs optic energy creating port energy;

an intensity controller positioned between said light guide and said port light guide, wherein said intensity controller controls an amount of optic energy received by said port light guide; and a heat dissipater positioned to dissipate heat generated by said light source.

6. A surgical lighting system for providing uniform and low-heat producing illumination, comprising:

a central column comprising a central column air passage to conduct heat so that heat within said central column may be drawn away from surgical operations;

a first articulating arm mechanically attached at a first end to said central column and mechanically attached at a second end to a first overhead light apparatus, providing aligned and substantially uniform optical energy to a first illumination region, wherein said first illumination region includes a first illumination pattern wherein said first articulating arm and said first overhead light apparatus have air passages interconnected to each other, wherein said air passages are additionally interconnected with said central column air passage so that heat from said first overhead light apparatus may be drawn through said central column;

a second articulating arm mechanically attached at a first end to said central column and mechanically attached at a second end to a second overhead light apparatus providing aligned substantially uniform optical energy to a second illumination region, wherein said second illumination region includes a second illumination pattern wherein said second articulating arm and second overhead light apparatus have air passages interconnected to each other, wherein said air passages are additionally interconnected with said central column air passage so that heat from said second overhead light apparatus may be drawn through said central column;

a third articulating arm attached at a first end to said central column and attached at a second end to a surgical light port apparatus, providing aligned optical energy to a port wherein said third articulating arm and surgical light port apparatus have air passages interconnected with each other, wherein said air passages are additionally interconnected with said central column air passage so that heat from said surgical light port apparatus may be drawn through said central column; and an exhaust port at the top of said central column where heat is drawn out of said central column and away from said surgical lighting system;

wherein said first and second articulating arms may be articulated so that said first illumination pattern overlaps with said second illumination pattern.

7. A surgical lighting system comprising:

a center column;

a light head attached to said center column by a support, wherein said support is attached to said center column by a hub and wherein said support is hollow;

an optical source positioned within said hub:

an elliptical back reflector positioned behind said optical source, wherein said wherein said elliptical reflector reflects optical energy generated by said optical source;

a heat absorptive filter positioned to receive optical energy generated from said optical source, wherein said heat absorptive filter removes heat power from optical energy received from said optical source;

a tamp exchanger, positioned within said center column and proximate to said optical source, wherein said optical source comprises a first lamp and a second lamp, wherein lamp exchanger removes said first lamp from said elliptical back reflector and inserts said second lamp into said elliptical back reflector;

a mixing pipe positioned to receive optical energy from said heat absorptive filter; an intensity controller positioned between said heat absorptive filter and said mixing pipe, wherein said intensity controller controls the amount of optical energy received by said mixing pipe and wherein said intensity controller includes highly reflective shutter blades; a continuous fiber bundle positioned to receive optical energy from said mixing pipe, wherein said continuous fiber bundle attaches to said light head, wherein said continuous fiber bundle delivers optical energy to said light head, wherein said continuous fiber bundle is positioned within said hollow support;

a heat dissipater positioned to dissipate heat generated by said optical source.

8. The surgical lighting system of claim 7, wherein said continuous bundle is within the range of eleven to thirteen feet in length.

* * * * *